United States Patent [19]

Junino et al.

[11] Patent Number: 5,002,585

[45] Date of Patent: * Mar. 26, 1991

[54] TRIALKOXY-SUBSTITUTED META-PHENYLENEDIAMINES, A PROCESS FOR THEIR PREPARATION, AND THEIR USE AS COUPLERS FOR THE OXIDATION DYEING OF KERATINOUS FIBRES AND IN PARTICULAR OF HUMAN HAIR

[75] Inventors: Alex Junino, Livry-Gargan; Jean J. Vandenbossche, Aulnay-sous-Bois; Herve Borowiak, Tremblay-les-Gonesse; Gerard Lang, Saint-Gratien, all of France

[73] Assignee: L'Oreal, Paris, France

[*] Notice: The portion of the term of this patent subsequent to Jan. 2, 2007 has been disclaimed.

[21] Appl. No.: 439,673

[22] Filed: Nov. 22, 1989

[30] Foreign Application Priority Data

Nov. 22, 1988 [LU] Luxembourg ............... 87396

[51] Int. Cl.$^5$ ............... A61K 7/13; C07C 215/80; C07C 215/78
[52] U.S. Cl. ............... 8/411; 8/408; 8/410; 8/412; 8/416; 8/421; 564/443
[58] Field of Search ............... 8/408, 410, 411, 412, 8/416, 421; 564/443

[56] References Cited

U.S. PATENT DOCUMENTS

| | | | |
|---|---|---|---|
| 4,125,367 | 11/1978 | Bugaut et al. | 8/411 |
| 4,171,203 | 10/1979 | Rose et al. | 8/416 |
| 4,566,876 | 1/1986 | Brown et al. | 8/411 |
| 4,865,618 | 9/1989 | Junino et al. | 8/411 |
| 4,865,619 | 9/1989 | Junino et al. | 8/412 |
| 4,891,045 | 1/1990 | Junino et al. | 8/411 |

FOREIGN PATENT DOCUMENTS 2542193 9/1984 France .

OTHER PUBLICATIONS

Chemical Abstract CA62: 2758b (1965).
Chemical Abstract CA64: 6611g (1966).
Brown et al., U.S. Statutory Invention Registration A726 1/2/1990.

*Primary Examiner*—Prince E. Willis
*Assistant Examiner*—Linda D. Skaling
*Attorney, Agent, or Firm*—Cushman, Darby & Cushman

[57] ABSTRACT

Trialkoxy-substituted meta-phenylenediamines, a process for their preparation, and their use as couplers for oxidation dying of keratinous fibres and in particulate of human hair.

1,3,5-trialkoxy-meta-phenylenediamine of formula:

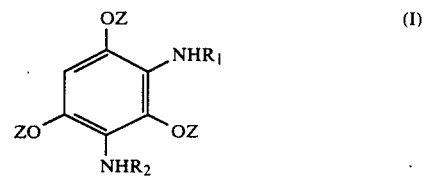

in which:

$R_1$ and $R_2$ denote, independently of each other, a hydrogen atom, an alkyl radical containing 1 to 4 carbon atoms or a mono- or polyhydroxyalkyl radical containing 2 or 3 carbon atoms, Z denotes an alkyl radical containing from 1 to 4 carbon atoms, provided that, when $R_1$ and $R_2$ simultaneously denote a hydrogen atom, Z does not denote the methyl radical, and the addition salts of this compound with an acid.

Process for the preparation of these compounds and their use as coupler in oxidation dying compositions for hair.

18 Claims, No Drawings

TRIALKOXY-SUBSTITUTED META-PHENYLENEDIAMINES, A PROCESS FOR THEIR PREPARATION, AND THEIR USE AS COUPLERS FOR THE OXIDATION DYEING OF KERATINOUS FIBRES AND IN PARTICULAR OF HUMAN HAIR

New trialkoxy-substituted meta-phenylenediamines, a process for their preparation, and their use as couplers for the oxidation dying of keratinous fibres and in particular of human hair.

The present invention relates to new meta-phenylenediamines, to the process for their preparation, the dye compositions for keratinous fibres and in particular for human hair, containing these meta-phenylenediamines acting as couplers, in combination with oxidation dye precursors, and to a dyeing process employing the said compositions.

It is known that it is common practice to employ, for dyeing keratinous fibres such as human hair or furs, dyeing compositions containing oxidation dye precursors and in particular para-phenylenediamines or ortho- or para-aminophenols, which are generally referred to by the term of oxidation bases.

It is also known that dye modifiers or couplers, and in particular meta-phenylenediamines, meta-aminophenols and meta-diphenols are employed in order to vary the shades obtained with these oxidation bases.

In the oxidizing alkaline media usually employed in oxidation dyeing, the para-phenylenediamines and para-aminophenols give rise to coloured indamines or indoanilines in the presence of couplers such as meta-phenylenediamines.

The indamines formed by meta-phenylenediamines and para-phenylenediamines in an oxidizing alkaline medium, and more particularly in the presence of hydrogen peroxide, impart very powerful blue colours to keratinous fibres. Indoanilines formed by meta-phenylenediamines and para-aminophenols in an oxidizing alkaline medium impart more or less purple red colours to keratinous fibres. Depending on the oxidation bases with which they are combined, meta-phenylenediamines can therefore give red or blue colours, which are two fundamental colours in hair dyeing, and are indispensable for obtaining not only blacks and greys but also coppery or ashen browns. The extremely important role played by the meta-phenylenediamines in oxidation hair dyeing can thus be appreciated.

It is important, moreover, that the oxidation bases and the couplers which are employed in oxidation dyeing compositions should impart to hair colours which are stable to light, to washing, to inclement weather and to perspiration. It is desirable that these colours be weakly selective or nonselective, that is to say that the colour obtained on natural hair and on hair sensitized by permanent-waving or bleaching be substantially identical. It is also necessary that these compounds should have the advantage of good safety.

Many couplers of the meta-phenylenediamine type substituted on the aromatic nucleus are already known. However, a large number of them do not meet the desired requirements.

The Applicant has just found new meta-phenylenediamines which combine a very good harmlessness with the dyeing qualities of a good coupler, and which can therefore be advantageously employed as couplers in combination with oxidation dye precursors, especially of the para type, in oxidation dyeing compositions for keratinous fibres.

"Oxidation dye precursors of the para type" means benzene-related or heterocyclic compounds substituted by two amino groups or by an amino group and a hydroxyl group in para positions relative to each other.

When combined with the majority of para-phenylenediamines in an oxidizing alkaline medium, the meta-phenylenediamines according to the invention impart to hair powerful blue colours which are more or less rich in green or in purple.

When combined with para-aminophenols in an oxidizing alkaline medium, the meta-phenylenediamines according to the invention impart to hair red colours which have good stability.

A subject of the present invention is therefore meta-phenylenediamines corresponding to formula (I) below or their addition salts with an acid:

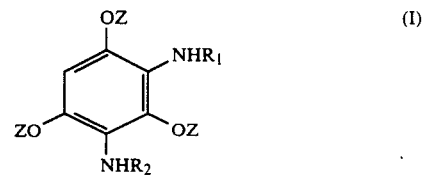

(I)

in which formula:

$R_1$ and $R_2$ denote, independently of each other, a hydrogen atom, an alkyl radical containing 1 to 4 carbon atoms or a mono- or polyhydroxyalkyl radical containing 2 or 3 carbon atoms.

Z denotes an alkyl radical containing from 1 to 4 carbon atoms, provided that when $R_1$ and $R_2$ simultaneously denote a hydrogen atom Z does not denote the methyl radical.

The process for the preparation of the compounds of formula (I) is also a subject of the present invention.

Another subject of the present invention is an oxidation hair dye composition comprising one or more couplers chosen from the compounds of formula (I) and their addition salts with acids, in combination with at least one oxidation dye precursor of the para type, in a cosmetically acceptable aqueous substrate.

The present invention is also aimed at the process for dyeing hair employing the above dye composition.

The compounds of formula (I) are prepared from 2,4-dinitro-1,3,5-trialkoxybenzenes of formula (II) below:

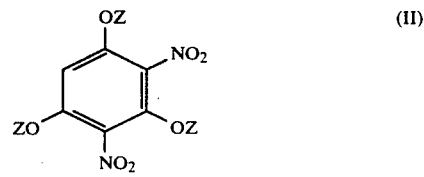

(II)

in which Z denotes a $C_1$–$C_4$ alkyl radical.

Depending on whether the radicals $R_1$ and $R_2$ are identical or different, the compounds (I) are prepared by one of the following reaction schemes:

1st case $R_1 = R_2$

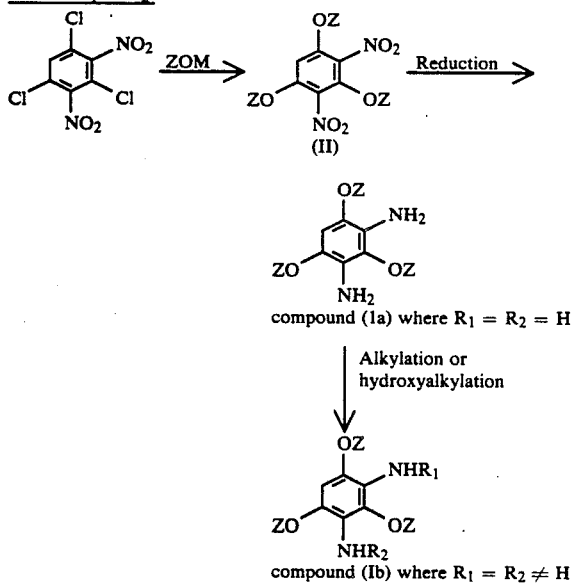

compound (Ia) where $R_1 = R_2 = H$

↓ Alkylation or hydroxyalkylation compound (Ib) where $R_1 = R_2 \neq H$

In the formulae above $R_1$, $R_2$ and Z have the meanings defined above.

The 2,4-dinitro-1,3,5-trialkoxybenzene (II) is prepared from 2,4-dinitro-1,3,5-trichlorobenzene by reaction with the alcoholate ZOM where M denotes an alkali or alkaline-earth metal, in the presence of the alcohol ZOH and of a solvent such as toluene or N-methylpyrrolidone.

Reduction, either with iron in the presence of acetic acid or with hydrogen in the presence of a catalyst such as palladium on charcoal, yields the 2,4-diamino-1,3,5-trialkoxybenzene of formula (Ia) where $R_1$ and $R_2$ both denote hydrogen ($R_1 = R_2 = H$).

Alkylation or hydroxyalkylation of the compound of formula (Ia) yields the compound of formula (Ib) where $R_1$ and $R_2$ both denote the same substituent other than hydrogen ($R_1 = R_2 \neq H$)

trialkoxybenzene is subjected to an alkylation or hydroxyalkylation of the amino group. The compound thus obtained is reduced with iron in the presence of acetic acid. The compound of formula (Ic) is thus obtained, where $R_2$ is hydrogen and $R_1$ is other than hydrogen ($R_1 \neq H$, $R_2 = H$). Alkylation or hydroxyalkylation of this compound of formula (Ic) yields the compound of formula (Id) where $R_1$ and $R_2$ are different from each other and other than hydrogen ($R_1 \neq R_2 \neq H$).

The preferred compounds of formula (I) are the following: —2-($\beta$-hydroxyethyl)amino-4-amino-1,3,5-trimethoxybenzene, —2,4-diamino-1,3,5-triethoxybenzene, —2-methylamino-4-amino-1,3,5-trimethoxybenzene, —2-methylamino-4-($\beta$-hydroxyethyl)amino-1,3,5-trimethoxybenzene, and their addition salts with an acid and in particular an inorganic acid such as hydrochloric, hydrobromic or sulphuric acid.

The hair dyeing compositions in accordance with the invention comprise at least one compound of formula (I) or one of its acid salts in combination with at least one oxidation dye precursor of the para type, in a cosmetically acceptable aqueous substrate. The compound of formula (I) or its salt acts as a coupler in this composition.

The oxidation dye precursor of the para type is chosen from benzene-related or heterocyclic derivatives such as, for example, pyridine, to which two amino groups or an amino group and a hydroxyl group are attached in the para position. These oxidation dye precursors may be present in the dye compositions in the form of free bases or in the form of addition salts of acids.

The oxidation dye precursors which are particularly preferred and capable of being employed in accordance with the invention are chosen from the paraphenylenediamines corresponding to the following general formula (III):

2nd case $R_1 \neq R_2$

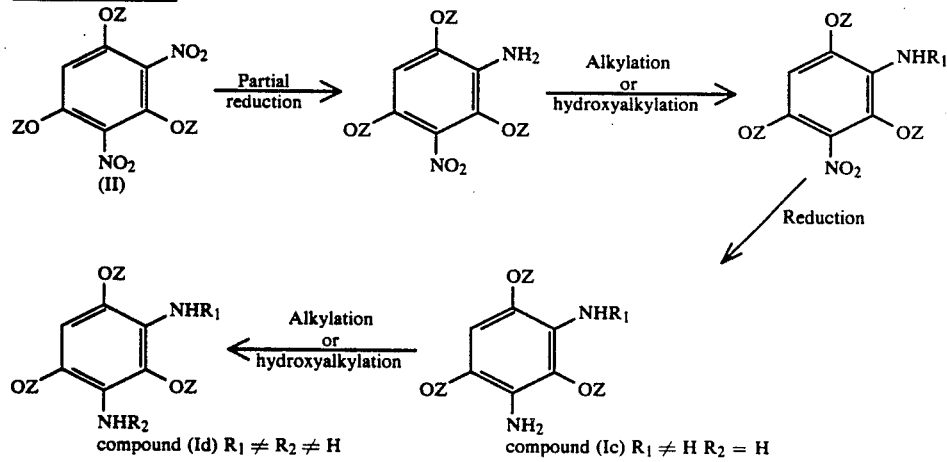

In a first stage the 2,4-dinitro-1,3,5-trialkoxybenzene (II) is subjected to a partial reduction which takes place by hydrogen transfer in the presence of a catalyst such as palladium on charcoal and of sodium hypophosphite as hydrogen donor, in tetrahydrofuran in the presence of water. in a second stage the 2-amino-4-nitro-1,3,5-

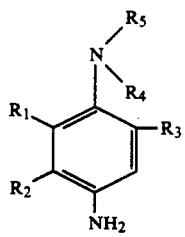

(III)

and the corresponding salts, in which formula $R_1$, $R_2$ and $R_3$ are identical or different and denote a hydrogen or halogen atom, and alkyl radical containing 1 to 4 carbon atoms, an alkoxy radical containing 1 to 4 carbon atoms, an alkoxy radical containing 1 to 4 carbon atoms, $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ having from 1 to 4 carbon atoms, or else $R_4$ and $R_5$ together with the nitrogen atom to which they are bonded can form a piperidino or morpholino heterocyclic ring, provided that $R_1$ or $R_3$ denotes a hydrogen atom when $R_4$ and $R_5$ do not denote a hydrogen atom.

Among the compounds of the formula (III) there may be mentioned: p-phenylenediamine, p-tolylenediamine, methoxy-para-phenylenediamine, chloro-para-phenylenediamine, 2,6-dimethyl-p-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di($\beta$-hydroxyethyl)-para-phenylenediamine, 3-methyl-4-amino-N,N-di($\beta$-hydroxyethyl)aniline, 3-chloro-4-amino-N,N-di($\beta$-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl, $\beta$-piperidinoethyl)aniline, 3-methyl-4-amino-N,N-(ethyl, $\beta$-piperidinoethyl)aniline, 4-amino-N,N-(ethyl, $\beta$-morpholinoethyl)aniline, 3-methyl-4-amino-N,N-(ethyl, $\beta$-morpholinoethyl)aniline, 4-amino-N,N-(ethyl, $\beta$-acetylaminoethyl)aniline, 4-amino-N-$\beta$-methoxyethylaniline, 3-methyl-4-amino-N,N-(ethyl, $\beta$-acetylaminoethyl)aniline, 4-amino-N,N-(ethyl, $\beta$-mesylaminoethyl)aniline, 3-methyl-4-amino-N,N-(ethyl, $\beta$-mesylaminoethyl)aniline, 4-amino-N,N-(ethyl, $\beta$-sulphoethyl)aniline, 3-methyl-4-amino-N,N-(ethyl, $\beta$-sulphoethyl)aniline, N-[(4'-amino)phenyl]morpholine, N-[(4'-amino)phenyl]piperidine, 2,3-dimethyl-p-phenylenediamine and isopropyl-p-phenylenediamine. These oxidation dye precursors of the para type may be introduced into the dye composition in the form of free base or in the form of salts such as in the form of hydrochloride, hydrobromide or sulphate.

The compound (I) or its salts can also be employed with p-aminophenols to give shades which are particularly stable to light, to inclement weather and to washing, after development in the presence of an oxidizing agent. Among the para-aminophenols there may be mentioned: p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-($\beta$-hydroxyethyl)-4-aminophenol, 2-methoxy-4-aminophenol and 3-methoxy-4-aminophenol.

The compound (I) and its salts can also be employed with heterocyclic para oxidation dye precursors, among which the may be mentioned 2,5-diaminopyridine, 2-hydroxy-5-aminopyridine and tetraaminopyrimidine.

The dye compositions according to the invention may also contain oxidation dye precursors of the ortho type, such as ortho-aminophenols and ortho-phenylenediamines. For example, 1-amino-2-hydroxybenzene, 6-methyl-1-hydroxy-2-aminobenzene and 4-methyl-1-amino-2-hydroxybenzene may be mentioned.

The dye compositions according to the invention containing the compound (I) or its salts may optionally contain other couplers which are known per se, such as meta-diphenols, meta-aminophenols, meta-phenylenediamines differing from formula 1, meta-acylaminophenols, meta-ureidophenols, meta-carbalkoxyaminophenols, $\alpha$-naphthol, couplers containing an active methylene group, such as $\beta$-ketonic compounds, and pyrazolones.

By way of example, there may be mentioned in particular, 2,4-dihydroxyphenoxyethanol, 2,4-dihydroxyanisole, meta-aminophenol, resorcinol, resorcinol monomethyl ether, 2-methyl-5-aminophenol, 2-methyl-5-N-($\beta$-hydroxyethyl)aminophenol, 2-methyl-5-N-($\beta$-mesylaminoethyl)aminophenol, 2,6-dimethyl-3-aminophenol, 6-hydroxybenzomorpholine, 2,4-diaminophenoxyethanol, 6-aminobenzomorpholine, 2-[N-($\beta$-hydroxyethyl)amino]-4-aminophenoxyethanol, 2-amino-4-N-($\beta$-hydroxyethyl)aminoanisole, (2,4-diamino)phenyl-$\beta$,$\gamma$-dihydroxypropyl ether, 2,4-diaminophenoxyethylamine, 3,4-methylenedioxyphenol, 3,4-methylenedioxyaniline and salts thereof.

As is well known, direct dyes such as azo or anthraquinone dyes or nitrobenzene derivatives may be added to these compositions with a view to tinting or enriching in highlights the colours contributed by the oxidation dye precursors.

The combined total of the para compounds and of the couplers employed in the dye compositions in accordance with the invention preferably represents from 0.1 to 7% by weight of the total weight of the said composition. The concentration of compound (I) may vary between 0.05 and 3.5% of the total weight of the composition.

The cosmetically acceptable aqueous substrate has a pH which can vary between 8 and 11, and is preferably between 9 and 11.

It is adjusted to the desired value with the aid of an alkalifying agent such as aqueous ammonia, alkali metal carbonates or alkanolamines such as mono-, di- or triethanolamine.

In their preferred embodiment, the dye compositions in accordance with the invention also contain anionic, cationic, nonionic or amphoteric surface-active agents or mixtures thereof. Among these surface-active agents there may be mentioned more particularly alkylbenzenesulphonates, alkylnaphthalenesulphonates, fatty alcohol sulphates, ether sulphates and sulphonates, quaternary ammonium salts such as trimethylcetylammonium bromide or cetylpyridinium bromide, optionally oxyethylenated fatty acid ethanolamides, polyoxyethylenated acids, alcohols and amines, polyglycerolated alcohols, polyoxyethylenated or polyglycerolated alkylphenols and polyoxyethylenated alkyl sulphates. The surface-active agents are present in the compositions in accordance with the invention in proportions of between 0.5 and 40% by weight, and preferably between 4 and 30% by weight relative to the total weight of the composition.

These compositions may also contain organic solvents to dissolve the compounds which might not be sufficiently soluble in water. Among these solvents there may be mentioned, by way of example, $C_1$–$C_4$ lower alkanols such as ethanol and isopropanol, aromatic alcohols such as benzyl alcohol and phenylethyl alcohol, glycerol, glycols or glycol ethers such as 2-butoxyethanol, ethylene glycol, propylene glycol, diethylene glycol mono-ethyl ether, diethylene glycol monomethyl ether, and similar products and mixtures thereof. These solvents are preferably present in a proportion of between 1 and 30% by weight, and in particular between 5 and 30% by weight relative to the total weight of the composition.

Thickening agents which may be added to the compositions in accordance with the invention are selected especially from the group consisting of sodium alginate, gum arabic, cellulose derivatives such as methyl cellulose, hydroxyethyl cellulose, hydroxypropyl cellulose, hydroxymethyl cellulose, carboxymethyl cellulose, acrylic acid polymers and xanthan gum. Inorganic thickening agents such as bentonite can also be employed. These thickening agents are preferably present in proportions of between 0.1 and 5% by weight, and in particular between 0.5 and 3% by weight relative to the total weight of the composition.

The compositions may contain antioxidant agents chosen, in particular, from sodium sulphite, thioglycolic acid, sodium bisulphite, ascorbic acid and hydroquinone. These antioxidant agents are present in the composition in proportions of between 0.05 and 1.5% by weight relative to the total weight of the composition.

Other adjuvants which may be employed in accordance with the invention are, for example, penetration agents, sequestering agents, buffers and perfumes.

The dye compositions in accordance with the invention may be presented in various forms, such as in the form of liquids, creams, gels or in any other suitable form for producing a dye for keratinous fibres and especially for human hair. They may also be packaged in aerosol bottles in the presence of a propellant agent.

The dye compositions in accordance with the invention, containing an oxidation dye precursor of the para type and the compound (I) or one of its salts, are employed in a process for oxidation hair dyeing.

In accordance with this process, the dye composition described above is mixed at the time of use with an oxidizing solution in a sufficient quantity, and the mixture obtained is then applied to hair.

The oxidizing solution contains oxidizing agents such as hydrogen peroxide, urea peroxide or their salts, such as ammonium persulphate. A 20-volume (6%) hydrogen peroxide solution is preferably employed.

The mixture obtained is applied to hair and left in place for 10 to 40 minutes, preferably 15 to 30 minutes, after which the hair is rinsed, is washed with a shampoo, is rinsed again and is dried.

Another process for making use of the compound (I) in accordance with the invention consists in dyeing hair by following a multistep procedure, according to which, in a first step, the para oxidation dye precursor is applied by means of an abovementioned composition and, in a second step, the compound (I) is applied. The oxidizing agent is present in the composition applied in the second step, or else is applied to hair itself in a third step, each of the compositions applied in the first and second step and, where applicable, the oxidizing agent applied in a third step, are left in contact with hair for 10 to 40 minutes, after which the hair is rinsed, washed with shampoo, rinsed again and dried.

The Examples which follow are used to illustrate the invention better, but do not in any case limit its scope.

EXAMPLE OF PREPARATION NO. 1

Preparation of 2-(β-hydroxyethyl)amino-4-amino-1,3,5-trimethoxybenzene dihydrochloride

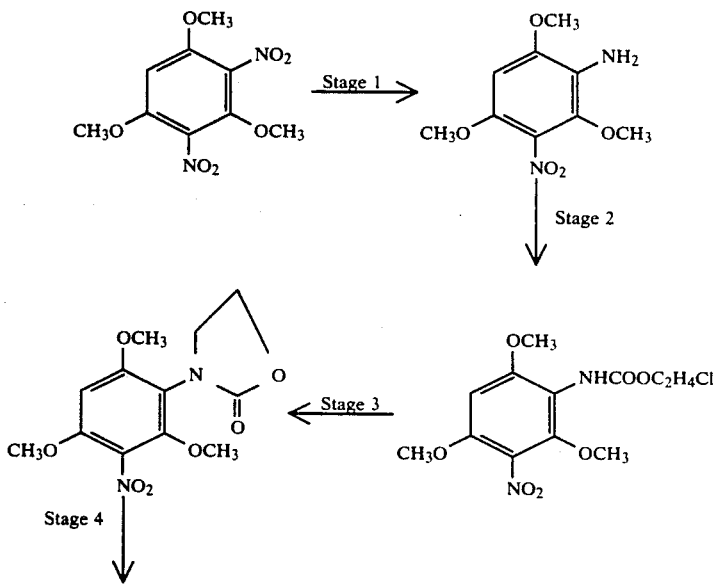

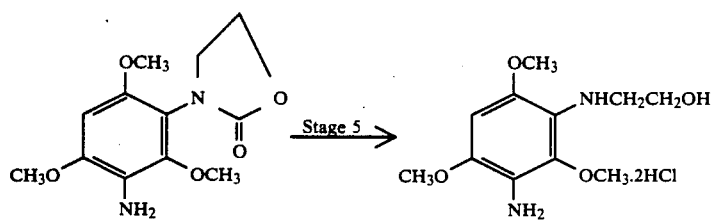

STAGE 1

Preparation of 2-amino-4-nitro-1,3,5-trimethoxybenzene

A suspension of 26 g of palladium on charcoal (10%) is refluxed in 1.3 l of tetrahydrofuran and 26 ml of water containing 1 mole (258 g) of 2,4-dinitro-1,3,5-trimethoxybenzene. A solution of 247 g of sodium hypophosphite in 260 ml of water is added to this suspension over 3 hours. Refluxing is continued for an additional 30 minutes. After cooling, the catalyst is removed by filtration and the aqueous phase by phase separation. The organic phase is concentrated under vacuum and is then poured onto ice. The expected product precipitates. It melts at 111° C.

Analysis of the product obtained, recrystallized from 96° ethanol, gives the following results:

|  | Calculated for $C_9H_{12}N_2O_5$ | Found |
| --- | --- | --- |
| C % | 47.37 | 47.31 |
| H % | 5.26 | 5.23 |
| N % | 12.28 | 12.36 |
| O % | 35.09 | 34.89 |

STAGE 2

Preparation of 2-(β-chloroethoxycarbonyl)amino-4-nitro-1,3,5-trimethoxybenzene 0.26 moles (60 g) of 2-amino-4-nitro-1,3,5-trimethoxybenzene are dissolved in 270 ml of dioxane. 26.3 g of calcium carbonate are added and the temperature is then raised to about 90° C. 0.34 moles (48.6 g) of chloroethyl chloroformate are then added with stirring. When the addition is complete, stirring is continued for additional 30 minutes at 90° C. The reaction mixture is diluted with 600 ml of iced water and is then acidified by adding 25 ml of concentrated hydrochloric acid. The precipitate obtained is filtered off and washed with water. After drying, it melts at 133° C.

Analysis of the product obtained, recrystallized from isopropanol, gives the following results:

|  | Calculated for $C_{12}H_{15}N_2O_7Cl$ | Found |
| --- | --- | --- |
| C % | 43.05 | 42.90 |
| H % | 4.48 | 4.32 |
| N % | 8.37 | 8.51 |
| O % | 33.48 | 33.21 |
| Cl % | 10.61 | 10.53 |

STAGE 3

Preparation of N-[(3'-nitro-2',4',6'-trimethoxy)phenyl]-1,3-oxazolidin-2-one 0.23 moles (80 g) of β-chloroethyl carbamate prepared in the preceding stage are heated to 65° C. in 240 ml of methanol. 0.25 moles of sodium methylate are added in solution at a concentration of 30% in methanol. Heating is continued for another 15 minutes after the end of the addition. The reaction mixture is diluted with 150 ml of iced water. The expected product precipitates. After reslurrying in 60 ml of ethanol, followed by drying, it melts at 178° C.

Analysis of the product obtained, recrystallized from ethanol, gives the following results:

|  | Calculated for $C_{12}H_{14}N_2O_7$ | Found |
| --- | --- | --- |
| C % | 48.32 | 48.37 |
| H % | 4.70 | 4.91 |
| N % | 9.39 | 9.48 |
| C % | 37.58 | 37.50 |

STAGE 4

Preparation of N-[(3'-amino-2',4',6'-trimethoxy)phenyl]-1,3-oxazolidin-2-one 120 g of iron powder reduced with hydrogen are added to 360 ml of water to which 6 ml of acetic acid have been added and which are preheated on a boiling water bath, followed by the addition in small portions, with stirring, of 0.2 moles (60 g) of the 1,2-oxazolidin-3-one prepared in the preceding stage. When the addition is complete, heating is continued for a further 30 minutes. After cooling, the reaction mixture is centrifuged. The ferric slurry containing the expected product is washed with water. The expected product is extracted from the ferric slurry using acetone. After recrystallization from isopropanol it melts at 162° C.

Elemental analysis of the product obtained gives the following results:

|  | Calculated for $C_{12}H_{16}N_2O_5$ | Found |
| --- | --- | --- |
| C % | 53.73 | 53.64 |
| H % | 5.97 | 6.01 |
| N % | 10.45 | 10.68 |
| O % | 29.85 | 30.07 |

STAGE 5

Preparation of
2-(β-hydroxyethyl)amino-4-amino-1,3,5-trimethoxybenzene dihydrochloride 0.1 mole (28 g) of the 1,3-oxazolidin-2-one prepared in the preceding stage is heated in 100 ml of 10N sodium hydroxide to which 30 ml of water and 70 ml of ethanol have been added. After 7 hours and 30 minutes' heating the reaction mixture is cooled. Alcohol is removed by evaporation. The expected product is extracted with ethyl acetate from the liquid residue. The hydrochloride is precipitated from the reaction mixture by adding a solution of hydrochloric ethanol.

Analysis of the product obtained gives the following results:

|  | Calculated for $C_{11}H_{20}N_2O_4Cl_2$ | Found |
| --- | --- | --- |
| C % | 41.91 | 41.83 |
| H % | 6.35 | 6.36 |
| N % | 8.89 | 9.03 |
| O % | 20.32 | 20.06 |
| Cl % | 22.52 | 22.37 |

EXAMPLE OF PREPARATION NO. 2

PREPARATION OF 2,4-DIAMINO 1,3,5-TRIETHOXYBENZENE

STAGE 1

Preparation of 2,4-dinitro 1,3,5-triethoxybenzene

A mixture comprising 0.18 mole (50 g) of 2,4-dinitro 1,3,5-trichlorobenzene and 250 ml of dioxane are heated at 70° C. 0.64 mole (219.9 g) of sodium ethylate in solution at a concentration of 20% in ethanol are then added while agitating. After the end of the addition the agitation is continued two more hours at 70° C. The reaction mixture is cooled and diluted with iced water. The expected product crystallizes and is separated by filtration. After drying it is recrystallized from ethanol. It melts at 105° C.

Elemental analysis of the product obtained gives the following results:

| Analysis | Calculated for $C_{12}H_6N_2O_7$ | Found |
| --- | --- | --- |
| % C | 48.00 | 48.02 |
| % H | 5.35 | 5.41 |
| % N | 9.33 | 9.41 |
| % O | 37.33 | 37.13 |

STAGE 2

Preparation of 2,4-diamino 1,3,5-triethoxybenzene dihydrochloride

A mixture comprising 0.1 mole (31.3 g) of 2,4-dinitro 1,3,5-triethoxybenzene, 120 ml of diglyme (diethyleneglycol dimethylether) and 6 ml water is heated at 80° C. in an autoclave during one hour in the presence of 4 g of 10% palladium on charcoal (catalyst) under hydrogen at a pressure of 1960 kPa (20 kg/cm²).

The catalyst is eliminated by filtration of the hot reaction medium.

The expected product precipitates from the filtrate after addition of 50 ml of concentrated hydrochloride acid. The thus prepared product is purified, after washing and hot drying under vacuum, by dissolution in 50 ml of boiling water, filtration of the hot aqueous solution and precipitation by addition of 100 ml of concentrated hydrochloric acid.

Analysis of the product obtained gives the following results:

| Analysis | Calculated for $C_{12}H_{22}N_2O_3Cl_2$ | Found |
| --- | --- | --- |
| C % | 46.01 | 46.08 |
| H % | 7.03 | 7.07 |
| N % | 8.94 | 8.78 |
| O % | 15.33 | 15.33 |
| Cl % | 22.68 | 22.80 |

EXAMPLE OF PREPARATION NO. 3

PREPARATION OF 2-METHYLAMINO-4-AMINO-1,4,5-TRIMETHOXYBENZENE

STAGE 1

Preparation of 2-formylamino-4-nitro-1,3,5-trimethoxybenzene

A mixture comprising 0.11 mole (26.6 g) of 2-amino-4-nitro-1,3,5-trimethoxybenzene and 55 ml of formic acid are refluxed during three hours. The reaction mixture is cooled and diluted with iced water. The expected product precipitates and is separated by filtration. After drying it is recrystallized from ethanol. It melts at 98° C.

Elemental analysis of the product obtained gives the following results:

|  | Calculated for $C_{10}H_{12}N_2O_6$ | Found |
| --- | --- | --- |
| % C | 46.88 | 47.01 |
| % H | 4.72 | 4.74 |
| % N | 10.93 | 10.89 |
| % O | 37.47 |  |

STAGE 2

Preparation of 2[(N-formyl, N-methyl)-amino]-4-nitro-1,3,5-trimethoxybenzene 0.058 mole (15 g) of 2-formylamino-4-nitro-1,3,5-trimethoxybenzene are dissolved in 75 ml of dimethylformamide at room temperature. 0.063 mole (11.84 g) of sodium methylate in solution at the concentration of 30% in methanol are added to the above mixture. 0.063 mole (7.94 g) of dimethylsulphate are added by small portions at a temperature comprised between 20° C. and 45° C. with agitation. After the end of the addition, agitation is continued 15 more minutes at 45° C. The mixture is diluted with 600 ml of iced water. The product is extracted with ethylacetate. After decantation of the aqueous phase, the organic phase is dried on sodium sulphate and concentrated under vacuum. The expected product is made into a paste with isopropylether and then dried. It melts at 110° C.

Elemental analysis gives the following results:

|  | Calculated for $C_{11}H_{14}N_2O_6$ | Found |
| --- | --- | --- |
| % C | 48.89 | 48.69 |
| % H | 5.22 | 5.22 |
| % N | 10.37 | 10.34 |
| % O | 35.52 |  |

STAGE 3

Preparation of 2-methylamino-4-amino-1,3,5-trimethoxybenzene dihydrochloride A suspension comprising 8 g of zinc powder, 0.2 g of ammonium chloride, 15 ml of ethanol and 5 ml of water is refluxed. 7.4 $10^{-3}$ moles (2 g) of 2[(N-formyl, N-methyl) amino]4-nitro-1,3,5-trimethoxybenzene are added in small portions. After the end of the addition the mixture is refluxed for another 5 minutes. Zinc salts are eliminated from the reaction mixture by filtration. The filtrate is diluted with 50 ml of concentrated hydrochloric acid and refluxed. The reaction mixture is evaporated under vacuum. The residue is dissolved and the expected product is separated.

Elemental analysis of the product obtained gives the following results:

|  | Calculated for $C_9H_{18}N_2O_3Cl_2$ | Found |
| --- | --- | --- |
| % C | 39.57 | |
| % H | 6.64 | |
| % N | 10.26 | |
| % O | 17.57 | |
| % Cl | 25.96 | |

| Dyeing Example 1 | |
| --- | --- |
| The following dyeing mixture is prepared: | |
| p-Phenylenediamine | 0.27 g |
| 2-(β-Hydroxyethyl)amino-4-amino-1,3,5-trimethoxybenzene dihydrochloride | 0.78 g |
| Oleyl alcohol polyglycerolated with 2 moles of glycerol | 4.5 g |
| Oleyl alcohol polyglycerolated with 4 moles of glycerol | 4.5 g |
| "Ethomeen O 12" - Armour Hess Chemical Ltd. (oleylamine oxyethylenated with 12 moles of ethylene oxide) | 4.5 g |
| "Comperlan KD" - Henkel (copra diethanolamide) | 9 g |
| Propylene glycol | 4 g |
| 2-Butoxyethanol | 8 g |
| 96° Ethanol | 6 g |
| "Masquol DTPA" - Protex (pentasodium salt of diethylenetriaminepentaacetic acid) | 2 g |
| Hydroquinone | 0.15 g |
| 35° Baume gravity sodium bisulphite solution | 1.3 g |
| 22° Baume gravity aqueous ammonia | 10 g |
| Water q.s. | 100 g |
| pH: 10.2 | |

100 g of 20 volume (6%) hydrogen peroxide are added at the time of use. When applied for 20 minutes at 35° C. to 90% naturally white hair, the mixture imparts a blueberry grey colour to it, after shampooing and rinsing.

| Dyeing Example 2 | |
| --- | --- |
| The following dyeing mixture is prepared: | |
| p-Aminophenol | 0.545 g |
| 2-(β-Hydroxyethyl)amino-4-amino-1,3,5-trimethoxybenzene dihydrochloride | 1.57 g |
| Oleyl alcohol polyglycerolated with 2 moles of glycerol | 4.5 g |
| Oleyl alcohol polyglycerolated with 4 moles of glycerol | 4.5 g |
| "Ethomeen O 12" - Armour Hess Chemical Ltd. (oleylamine oxyethylenated with 12 moles of EO) | 4.5 g |
| "Comperlan KD" - Henkel (copra diethanolamide) | 9 g |
| Propylene glycol | 4 g |
| 2-Butoxyethanol | 8 g |
| 96° Ethanol | 6 g |
| "Masquol DTPA" - Protex (pentasodium salt of diethylenetriaminepentaacetic acid) | 2 g |
| Hydroquinone | 0.15 g |
| 35° Baume gravity sodium bisulphite solution | 1.3 g |
| 22° Baume gravity aqueous ammonia | 10 g |
| Water q.s. | 100 g |
| pH: 10.2 | |

100 g of 20 volume (6%) hydrogen peroxide are added at the time of use. When applied for 20 minutes at 35° C. to bleached hair, the mixture gives it a raspberry colour, after shampooing and rinsing.

| Dyeing Example 3 | |
| --- | --- |
| The following dyeing mixture is prepared: | |
| 2,4-diamino 1,3,5-triethoxybenzene dihydrochloride | 0.78 g |
| p-phenylenediamine | 0.27 g |
| Oleyl alcohol glycerolated with 2 moles of glycerol | 4.5 g |
| Oleyl alcohol glycerolated with 4 moles of glycerol | 4.5 g |
| "Ethomeen O 12" - Armour Hess Chemical Ltd. (oleylamine oxyethylenated with 12 moles of ethyleneoxide) | 4.5 g |
| "Comperlan KD" - Henkel (copra diethanolamide) | 9 g |
| Propyleneglycol | 4 g |
| 2-butoxyethanol | 8 g |
| "Masquol DTPA" - Protex (pentasodium salt of diethylenetriamine pentaacetic acid) | 2 g |
| Hydroquinone | 0.15 g |
| 35° Baume gravity sodium bisulfite solution | 1.3 g |
| 22° Baume gravity aqueous ammonia | 10 g |
| Water q.s. | 100 g |
| pH: 10 | |

100 g of 20 volume (6%) hydrogen peroxide are added at the time of use. When applied for 20 minutes at 35° C. to bleached hair, the mixture imparts a dark purple blue color to it, after shampooing and rinsing.

| Dyeing Example 4 | |
| --- | --- |
| The following dyeing mixture is prepared: | |
| 2-methylamino-4-amino 1,3,5-triethoxybenzenedihydrochloride | 0.71 g |
| p-phenylenediamine | 0.27 g |
| Oleyl alcohol glycerolated with 2 moles of glycerol | 4.5 g |
| Oleyl alcohol glycerolated with 4 moles of glycerol | 4.5 g |
| "Ethomeen O 12" - Armour Hess Chemical Ltd. (oleylamine oxyethylenated with 12 moles of ethyleneoxide) | 4.5 g |
| "Comperlan KD" - Henkel (copra diethanolamide) | 9 g |
| Propyleneglycol | 4 g |
| 2-butoxyethanol | 8 g |
| "Masquol DTPA" - Protex (pentasodium salt of diethylenetriamine pentaacetic acid) | 2 g |
| Hydroquinone | 0.15 g |
| 35° Baume gravity sodium bisulfite solution | 1.3 g |
| 22° Baume gravity aqueous ammonia | 10 g |
| Water q.s. | 100 g |
| pH: 10 | |

100 g of 20 volume (6%) hydrogen peroxide are added at the time of use. When applied for 20 minutes at 35° C. to bleached hair, the mixture imparts a dark purple blue color to it, after shampooing and rinsing.

We claim:

1. 1,3,5-trialkoxy-meta-phenylenediamine having the formula

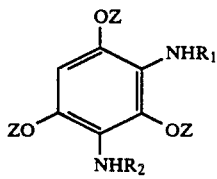

wherein $R_1$ and $R_2$, each independently, represent hydrogen, alkyl containing 1–4 carbon atoms or mono- or polyhydroxyalkyl having 2–3 carbon atoms, Z represents alkyl containing 1–4 carbon atoms with the proviso that when $R_1$ and $R_2$ simultaneously represent hydrogen, Z is other than methyl, and the addition salt of said 1,3,5-trialkoxy-meta-phenylenediamine with an acid.

2. The compound of claim 1 selected from the group consisting of 2-(β-hydroxyethyl) amino-4-amino-1,3,5-trimethoxybenzene, 2,4-diamino-1,3,5-triethoxybenzene, 2-methylamino-4-amino-1,3,5-trimethoxybenzene, 2-methylamino-4-(β-hydroxyethyl) amino-1,3,5-trimethoxybenzene, and the addition salt thereof with an acid.

3. A hair dyeing composition comprising in a cosmetically acceptable vehicle, at least one compound of formula I or the addition salt thereof of claim 1 in an amount ranging from 0.05 to 3.5 percent by weight based on the total weight of said composition, in combination with at least one oxidation dye precursor of the para type, the combined total amount of the compound of formula I and said oxidation dye precursor ranging from 0.1 to 7 percent by weight based on the total weight of said composition.

4. The hair dye composition of claim 3 wherein said oxidation precursor of the para type is selected from a p-phenylenediamine, a p-aminophenol, a p-heterocyclic compound and a mixture thereof.

5. The hair dye composition of claim 25 wherein said p-phenylenediamine has the formula:

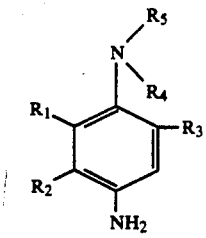

wherein $R_1$, $R_2$ and $R_3$, each independently, represent hydrogen, halogen, alkyl having 1–4 carbon atoms or alkoxy having 1–4 carbon atoms, $R_4$ and $R_5$, each independently, represent hydrogen, alkyl, hydroxyalkyl, alkoxyalkyl, carbamylalkyl, mesylaminoalkyl, acetylaminoalkyl, ureidoalkyl, carbethoxyaminoalkyl, piperidino alkyl or morpholinoalkyl, the alkyl or alkoxy groups represented by $R_4$ and $R_5$ containing 1–4 carbon atoms, or $R_4$ and $R_5$ together with the nitrogen atom to which they are attached form a piperidino or morpholino heterocyclic ring, with the proviso that $R_1$ or $R_3$ represents hydrogen when $R_4$ and $R_5$ do not represent hydrogen, said phenylenediamine being in the form of a free base or in the form of a cosmetically acceptable salt.

6. The hair dye composition of claim 5 which contains at least one p-phenylenediamine selected from the group consisting of p-phenylenediamine,
p-tolyenediamine,
methoxy-para-phenylenediamine,
chloro-para-phenylenediamine,
2,6-dimethyl-p-phenylenediamine,
2,5-dimethyl-p-phenylenediamine,
2-methyl-5-methoxy-p-phenylenediamine,
2,6-dimethyl-5-methoxy-p-phenylenediamine,
N,N-dimethyl-p-phenylenediamine,
3-methyl-4-amino-N,N-diethylaniline,
N,N-di-β-hydroxyethyl)-p-phenylenediamine,
3-methyl-4-amino-N,N-di(β-hydroxyethyl)aniline,
3-chloro-4-amino-N,N-di(β-hydroxyethyl)aniline,
4-amino-N,N-(ethyl,carbamylmethyl)aniline,
3-methyl-4-amino-N,N-(ethyl,carbamylmethyl)aniline,
4-amino-N,N-(ethyl,β-piperidinoethyl)aniline,
3-methyl-4-amino-N,N-(ethyl,β-piperidinomethyl)aniline,
4-amino-N,N-(ethyl,β-morpholinoethyl)aniline,
3-methyl-4-amino-N,N-(ethyl,β-morpholinoethyl)aniline,
4-amino-N-β-methoxyethylaniline,
3-methyl-4-amino-N,N-(ethyl,β-acetylaminoethyl)aniline,
4-amino-N,N-(ethyl,β-mesylaminoethyl)aniline,
3-methyl-4-amino-N,N-(ethyl,β-mesylaminoethyl)aniline,
4-amino-N,N-(ethyl,β-sulphoethyl)aniline,
3-methyl-4-amino-N,N-(ethyl,β-sulphoethyl)aniline,
N-[(4'-amino)phenyl]morpholine,
N-[(4'-amino)phenyl]piperidine,
2,3-dimethyl-p-phenylenediamine and
isopropyl-p-phenylenediamine, in the form of free base or in the form of a cosmetically acceptable salt.

7. The hair dye composition of claim 6 which contains at least one p-aminophenol selected from the group consisting of p-aminophenol,
2-methyl-4-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2,5-dimethyl-4-aminophenol,
2-hydroxymethyl-4-aminophenol,
2-(β-hydroxyethyl)-4-aminophenol,
2-methoxy-4-aminophenol and
3-methoxy-4-aminophenol.

8. The hair dye composition of claim 5 wherein said oxidation dye precursor of the para type is a heterocyclic para compound selected from 2,5-diaminopyridine, 2-hydroxy-5-aminopyridine and tetraaminopyridine.

9. The hair dye composition of claim 3 which also contains at least one of a meta-diphenol, a meta-aminophenol, meta-phenylenediamine having a formula other than formula I, a meta-acylaminophenol, a meta-ureidophenol, a meta-carbalkoxyaminophenol, α-naphthol, a β-ketonic compound and a pyrazolone.

10. The hair dye composition of claim 3 which also contains a dye precursor of the ortho type selected from the group consisting of an ortho-aminophenol and an orthophenylenediamine.

11. The hair dye composition of claim 3 which also contains a direct dye selected from an azo dye, an anthraquinone dye and a nitrobenzene dye derivative.

12. The hair dye composition of claim 3 having a pH ranging from 8 to 11.

13. The hair dye composition of claim 3 which contains from 1 to 40 percent by weight of an organic solvent selected from a lower alkanol, an aromatic alcohol, glycerol, a glycol, a glycol ether, or a mixture thereof.

14. The hair dye composition of claim 3 which also contains from 0.5 to 40 percent by weight of at least one anionic, cationic, nonionic or amphoteric surface-active agent, or a mixture thereof.

15. The hair dye composition of claim 3 which also contains at least one cosmetic adjuvant selected from a thickener, an antioxidant agent, a penetration agent, a sequestering agent, a buffer, a perfume, an alkalizing agent and a propellant.

16. An oxidation hair dyeing process comprising
mixing, at the time of use, the hair dye composition of claim 3 with a sufficient amount of an oxidizing solution so as to oxidize the oxidation dye precursor of the para type present in said hair dye composition,
applying the resulting mixture to the hair,
permitting said mixture to remain in contact with the hair for a period of time ranging from 10 to 40 minutes,
rinsing the hair,
washing the hair with water, and
drying the hair.

17. An oxidation hair dyeing process comprising
(a) applying to the hair a hair dye composition (A) containing at least one oxidation dye precursor of the para type selected from a p-phenylenediamine, a p-aminophenol, a p-heterocyclic compound or a mixture thereof, and permitting said composition (A) to remain in contact with the hair for a period of time ranging from 10 to 40 minutes,
(b) applying to said hair a dye composition (B) containing
(i) at least one compound having the formula

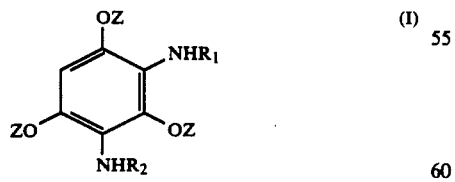

wherein
$R_1$ and $R_2$, each independently, represent hydrogen, alkyl containing 1-4 carbon atoms or mono- or polyhydroxyalkyl having 2-3 carbon atoms,
Z represents alkyl containing 1-4 carbon atoms with the proviso that when $R_1$ and $R_2$ simultaneously represent hydrogen, Z is other than methyl, or the acid addition salt of the compound of formula I with an acid in an amount ranging from 0.05 to 3.5 percent by weight based on the total weight of said composition B, the combined total amount of the compound of formula I and said oxidation dye precursor of step (a) ranging from 0.1 to 7 percent by weight based on the total weight of hair dye compositions (A) and (B), and
(ii) an oxidizing solution in an amount sufficient to oxidize said oxidation dye precursor of the para type, and permitting said composition (B) to remain in contact with the hair for a period of time ranging from 10 to 40 minutes,
(c) rinsing the hair,
(d) washing the hair with a shampoo,
(e) rinsing the hair, and
(f) drying the hair.

18. An oxidation hair dyeing process comprising
(a) applying to the hair a hair dye composition (A) containing at least one oxidation dye precursor of the para type selected from a p-phenylenediamine, a p-aminophenol, a p-heterocyclic compound or a mixture thereof, and permitting said composition (A) to remain in contact with the hair for a period of time ranging from 10 to 40 minutes,
(b) applying to the hair a hair dye composition (B) containing at least one compound having the formula

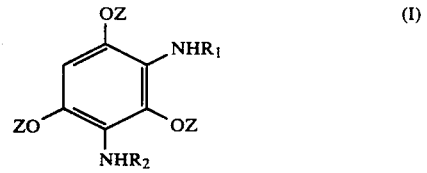

wherein
$R_1$ and $R_2$, each independently, represent hydrogen, alkyl containing 1-4 carbon atoms or mono- or polyhydroxyalkyl having 2-3 carbon atoms,
Z represents alkyl containing 1-4 carbon atoms with the proviso that when $R_1$ and $R_2$ simultaneously represent hydrogen, Z is other than methyl, or the addition salt of the compound of formula I with an acid in an amount ranging from 0.05 to 3.5 percent by weight based on the total weight of said composition (B), the combined total amount of the compound of formula I and said oxidation dye precursor of step (a) ranging from 0.1 to 7 percent by weight based on the total weight of hair dye compositions (A) and (B), and permitting said composition (B) to remain in contact with the hair for a period of time ranging from 10 to 40 minutes,
(c) applying to the hair an oxidizing solution (C) in an amount sufficient to oxidize said oxidation dye precursor applied to the hair in step (a) and permitting said oxidizing solution (C) to remain in contact with the hair for a period of time ranging from 10 to 40 minutes,
(d) rinsing the hair,
(e) washing the hair with a shampoo,
(f) rinsing the hair and
(g) drying the hair.

* * * * *

UNITED STATES PATENT AND TRADEMARK OFFICE
CERTIFICATE OF CORRECTION

PATENT NO. : 5,002,585
DATED : March 26, 1991
INVENTOR(S) : Alex Junino et al It is certified that error appears in the above-identified patent and that said Letters Patent is hereby corrected as shown below:

Column 15, line 50, "claim 25" should read --claim 4--.

Signed and Sealed this

Twenty-first Day of September, 1993

Attest:

BRUCE LEHMAN

*Attesting Officer*          *Commissioner of Patents and Trademarks*